United States Patent
Desjardins et al.

(10) Patent No.: US 10,864,194 B2
(45) Date of Patent: Dec. 15, 2020

(54) METHODS FOR TREATING HETEROTOPIC OSSIFICATION

(71) Applicant: Clementia Pharmaceuticals Inc., Montreal (CA)

(72) Inventors: Clarissa Desjardins, Westmount (CA); Donna Roy Grogan, Boston, MA (US); Jeffrey Neal Packman, Weston, MA (US); Mark Harnett, Stow, MA (US)

(73) Assignee: Clementia Pharmaceuticals Inc., Montreal (CA)

( * ) Notice: Subject to any disclaimer, the term of this patent is extended or adjusted under 35 U.S.C. 154(b) by 0 days.

(21) Appl. No.: 16/308,012

(22) PCT Filed: Jun. 8, 2017

(86) PCT No.: PCT/CA2017/050701
§ 371 (c)(1),
(2) Date: Dec. 7, 2018

(87) PCT Pub. No.: WO2017/210792
PCT Pub. Date: Dec. 14, 2017

(65) Prior Publication Data
US 2019/0216781 A1 Jul. 18, 2019

Related U.S. Application Data

(60) Provisional application No. 62/347,381, filed on Jun. 8, 2016.

(51) Int. Cl.
| | | |
|---|---|---|
| *A61K 31/415* | (2006.01) | |
| *A61P 19/08* | (2006.01) | |
| *A61P 31/00* | (2006.01) | |
| *A61P 19/04* | (2006.01) | |
| *A61K 9/00* | (2006.01) | |
| *A61K 45/06* | (2006.01) | |

(52) U.S. Cl.
CPC .......... *A61K 31/415* (2013.01); *A61K 9/0053* (2013.01); *A61P 19/04* (2018.01); *A61P 19/08* (2018.01); *A61P 31/00* (2018.01); *A61K 9/0014* (2013.01); *A61K 45/06* (2013.01)

(58) Field of Classification Search
CPC .................................................. A61K 31/415
USPC ...................................................... 514/406
See application file for complete search history.

(56) References Cited

U.S. PATENT DOCUMENTS

| | | | |
|---|---|---|---|
| 5,624,957 A | 4/1997 | Swann et al. | |
| 5,760,084 A | 6/1998 | Swann et al. | |
| 5,824,685 A | 10/1998 | Campochiaro et al. | |
| 6,187,950 B1 | 2/2001 | Song et al. | |
| 6,204,288 B1 | 3/2001 | Pershadsingh et al. | |
| 6,313,168 B1 | 11/2001 | Pacifici et al. | |
| 6,777,418 B2 | 8/2004 | Lapierre et al. | |
| 6,838,472 B2 | 1/2005 | Klaus et al. | |
| 6,844,466 B2 | 1/2005 | Belloni et al. | |
| 7,345,931 B2 | 3/2008 | Partsch et al. | |
| 7,547,687 B2 | 6/2009 | Reading et al. | |
| 9,045,484 B2 | 6/2015 | Yu et al. | |
| 9,314,439 B2 | 4/2016 | Iwamoto et al. | |
| 9,492,431 B2 | 11/2016 | Kimura | |
| 9,750,721 B2 | 9/2017 | Kimura | |
| 9,789,074 B2 | 10/2017 | Iwamoto et al. | |
| 2002/0082265 A1 | 6/2002 | Lapierre et al. | |
| 2003/0113913 A1 | 6/2003 | Purton et al. | |
| 2003/0114482 A1 | 6/2003 | Pacifici et al. | |
| 2003/0125252 A1 | 7/2003 | Underhill et al. | |
| 2005/0271705 A1 | 12/2005 | Hughes et al. | |
| 2006/0210638 A1 | 9/2006 | Liversidge et al. | |
| 2009/0074789 A1 | 3/2009 | Sabbadini et al. | |
| 2009/0176862 A1 | 7/2009 | Chandraratna et al. | |
| 2009/0214493 A1 | 8/2009 | Pittenger et al. | |
| 2009/0281184 A1 | 11/2009 | Sawada et al. | |
| 2011/0076318 A1 | 3/2011 | Hughes et al. | |
| 2012/0077786 A1 | 3/2012 | Byron et al. | |
| 2012/0277156 A1* | 11/2012 | Gross | A61K 31/167 514/16.7 |
| 2013/0189319 A1 | 7/2013 | Cook et al. | |
| 2014/0220154 A1* | 8/2014 | Regard | A61K 31/015 424/623 |
| 2014/0303223 A1 | 10/2014 | Iwamoto et al. | |

(Continued)

FOREIGN PATENT DOCUMENTS

| | | | |
|---|---|---|---|
| WO | WO-2001/080894 A2 | 11/2001 | |
| WO | WO-2005/115304 A2 | 12/2005 | |

(Continued)

OTHER PUBLICATIONS

"A Phase 2 Randomized, Double-Blind, Placebo-Controlled Efficacy and Safety Study of a RAR gamma-Specific Agonist (Palovarotene) in the Treatment of Preosseous Flare-ups in Subjects with Fibrodysplasia Ossificans Progressiva (FOP)," U.S. National Library of Medicine, < https://clinicaltrials.gov/ct2/history/NCT02190747?V_12=View#StudyPageTop>, dated Aug. 25, 2015, retrieved on Dec. 17, 2019 (5 pages).

"A Phase 2 Randomized, Double-Blind, Placebo-Controlled Efficacy and Safety Study of a RAR gamma-Specific Agonist (Palovarotene) in the Treatment of Preosseous Flare-ups in Subjects with Fibrodysplasia Ossificans Progressiva (FOP)," U.S. National Library of Medicine, < https://clinicaltrials.gov/ct2/history/NCT02190747?V_16=View#StudyPageTop>, dated Mar. 1, 2016, retrieved on Dec. 17, 2019 (5 pages).

"A Phase 2 Randomized, Double-Blind, Placebo-Controlled Efficacy and Safety Study of a RAR gamma-Specific Agonist (Palovarotene) in the Treatment of Preosseous Flare-ups in Subjects with Fibrodysplasia Ossificans Progressiva (FOP)," U.S. National Library of Medicine, < https://clinicaltrials.gov/ct2/history/NCT02190747?V_1=View#StudyPageTop>, dated Jul. 14, 2014, retrieved on Dec. 17, 2019 (5 pages).

(Continued)

*Primary Examiner* — Raymond J Henley, III
(74) *Attorney, Agent, or Firm* — Clark & Elbing LLP

(57) ABSTRACT

The invention features dosing regimens and pharmaceutical formulations for oral administration of palovarotene. The dosing regimens can reduce heterotopic ossification, reduce the number of flare-ups, and/or reduce the severity of flare-ups in subjects suffering from fibrodysplasia ossificans progressiva.

30 Claims, 3 Drawing Sheets

(56) References Cited

U.S. PATENT DOCUMENTS

| | | |
|---|---|---|
| 2014/0363402 A1 | 12/2014 | Iwamoto et al. |
| 2015/0290172 A1 | 10/2015 | Kimura |
| 2016/0120843 A1 | 5/2016 | Kimura |
| 2017/0065562 A1 | 3/2017 | Kimura |
| 2017/0182079 A1* | 6/2017 | Levi ............... A61K 31/198 |

FOREIGN PATENT DOCUMENTS

| | | |
|---|---|---|
| WO | WO-2010/071583 A1 | 6/2010 |
| WO | WO-2010/088735 A1 | 8/2010 |
| WO | WO-2012/030919 A2 | 3/2012 |
| WO | WO-2012/125724 A1 | 9/2012 |
| WO | WO-2012/129562 A2 | 9/2012 |
| WO | WO-2014/138088 A1 | 9/2014 |
| WO | WO-2014/160203 A2 | 10/2014 |
| WO | WO-2016/054406 A1 | 4/2016 |
| WO | WO-2017/070194 A1 | 4/2017 |

OTHER PUBLICATIONS

"A Phase 2 Randomized, Double-Blind, Placebo-Controlled Efficacy and Safety Study of a RAR gamma-Specific Agonist (Palovarotene) in the Treatment of Preosseous Flare-ups in Subjects with Fibrodysplasia Ossificans Progressiva (FOP)," U.S. National Library of Medicine, <https://clinicaltrials.gov/ct2/history/NCT02190747?V_17=View#StudyPageTop>, dated Apr. 4, 2016, retrieved on Sep. 30, 2019 (5 pages).

"A Phase 2, Open-Label Extension, Efficacy and Safety Study of a RAR gamma Specific Agonist (Palovarotene) in the Treatment of Preosseous Flare-ups in Subjects With Fibrodysplasia Ossificans Progressiva (FOP)," U.S. National Library of Medicine, < https://clinicaltrials.gov/ct2/history/NCT02279095?V_7=View#StudyPageTop>, dated Jan. 7, 2016, retrieved on Dec. 17, 2019 (5 pages).

"A Phase 2, Open-Label Extension, Efficacy and Safety Study of a RAR gamma Specific Agonist (Palovarotene) in the Treatment of Preosseous Flare-ups in Subjects With Fibrodysplasia Ossificans Progressiva (FOP)," U.S. National Library of Medicine, < https://clinicaltrials.gov/ct2/history/NCT02279095?V_8=View#StudyPageTop>, dated Jun. 9, 2016, retrieved on Dec. 17, 2019 (5 pages).

"A Phase 2, Open-Label Extension, Efficacy and Safety Study of a RAR gamma Specific Agonist (Palovarotene) in the Treatment of Preosseous Flare-ups in Subjects With Fibrodysplasia Ossificans Progressiva (FOP)," U.S. National Library of Medicine, < https://clinicaltrials.gov/ct2/history/NCT02279095?V_14=View#StudyPageTop>, dated Feb. 10, 2017, retrieved on Dec. 17, 2019 (5 pages).

"A Phase 2, Open-Label Extension, Efficacy and Safety Study of a RAR gamma Specific Agonist (Palovarotene) in the Treatment of Preosseous Flare-ups in Subjects With Fibrodysplasia Ossificans Progressiva (FOP)," U.S. National Library of Medicine, < https://clinicaltrials.gov/ct2/history/NCT02279095?V_1=View#StudyPageTop>, dated Oct. 28, 2014, retrieved on Dec. 20, 2019 (5 pages).

"Palovarotene drug may prevent multiple musculoskeletal problems linked with FOP," News Medical Life Sciences, <https://www.news-medical.net/news/20160415/Palovarotene-drug-may-prevent-multiple-musculoskeletal-problems-linked-with-FOP.aspx>, dated Apr. 15, 2016 (3 pages).

Brennan et al., "Mast cell inhibition as a therapeutic approach in fibrodysplasia ossificans progressiva (FOP)," Bone. http://dx.doi.org/10.1016/j.bone.2017.08.023 (2017) (8 pages).

Cahill et al., "Kit Inhibition by Imatinib in Patients with Severe Refractory Asthma," available in PMC Nov. 18, 2017, published in final edited form as: N Engl J Med. 376(20):1911-20 (2017) (17 pages).

Chakkalakal et al., "Palovarotene Inhibits Heterotopic Ossification and Maintains Limb Mobility and Growth in Mice With the Human ACVR1(R206H) Fibrodysplasia Ossificans Progressiva (FOP) Mutation," J Bone Miner Res. 31(9):1666-75 (2016).

Ciavarella et al., "20 novel point mutations and one large deletion in EXT1 and EXT2 genes: report of diagnostic screening in a large Italian cohort of patients affected by hereditary multiple exostosis," Gene. 515(2):339-48 (2013) (10 pages).

Clement et al., "Use of imatinib in the prevention of heterotopic ossification," HSS J. 9(2):166-70 (2013).

Convente et al., "Depletion of Mast Cells and Macrophages Impairs Heterotopic Ossification in an Acvr1 R206H Mouse Model of Fibrodysplasia Ossificans Progressiva," J Bone Miner Res. 33(2):269-82 (2018).

Cuellar et al., "Cell biology of osteochondromas: bone morphogenic protein signalling and heparan sulphates," Int Orthop. 37(8):1591-6 (2013).

Czajka et al., "What is the Proportion of Patients With Multiple Hereditary Exostoses Who Undergo Malignant Degeneration?" Clin Orthop Relat Res. 473(7):2355-61 (2015).

Danziger et al., "Automated site-directed drug design: a general algorithm for knowledge acquisition about hydrogen-bonding regions at protein surfaces," Proc R Soc Lond B Biol Sci. 236(1283):101-13 (1989).

Di Rocco et al., "Selective RAR gamma agonist blocks heterotopic ossification and promotes skeletal muscle repair," ASBMR Oct. 4, 2013, (Abstract only) (2 pages).

Di Rocco et al., "Selective retinoic acid receptor gamma agonists promote repair of injured skeletal muscle in mouse," Am J Pathol. 185(9):2495-504 (2015).

Duncan et al., "The link between heparan sulfate and hereditary bone disease: finding a function for the EXT family of putative tumor suppressor proteins," J Clin Invest. 108(4):511-6 (2001).

Einhorn et al., "Bone regeneration: new findings and potential clinical applications," J Am Acad Orthop Surg. 9(3):157-65 (2001).

English translation of Japanese Patent Application No. 2005-206544, dated Nov. 23, 2015 (14 pages).

English Translation of Notice of Defects in Patent for Israeli Patent Application No. 224973, dated Dec. 16, 2015 (2 pages).

English translation of Office Action for Chilean Patent Application No. 201300580, dated Dec. 27, 2017 (6 pages).

English Translation of Office Action for Eurasian Patent Applicaiton No. 201370051, dated Jun. 1, 2015 (4 pages).

Examination Report for Australian Patent Application No. 2015200760, dated Mar. 2, 2016 (4 pages).

Extended European Search Report for European Patent Application No. 11822537.4, dated Feb. 7, 2014 (10 pages).

First Examination Report for New Zealand Patent Application No. 706089, dated Mar. 25, 2015 (3 pages).

Further Examination Report for New Zealand Patent Application No. 607547, dated Mar. 25, 2015 (2 pages).

Further Examination Report for New Zealand Patent Application No. 607547, dated Nov. 19, 2014 (2 pages).

Gannon et al., "Mast cell involvement in fibrodysplasia ossificans progressiva," Hum Pathol. 32(8):842-8 (2001).

Halevy et al., "Retinoic acid induces adult muscle cell differentiation mediated by the retinoic acid receptor-alpha." J Cell Physiol. 154(3):566-72 (1993).

Hesse, "Muscle and Bone: Combating the Evil Side of the Connection," J Bone Miner Res. 31(9):1647-51 (2016).

Hopkins, "Inhibitors of the bone morphogenetic protein (BMP) signaling pathway: a patent review (2008-2015)," Expert Opin Ther Pat. 26(10):1115-28 (2016) (15 pages).

International Search Report and Written Opinion for International Application No. PCT/CA2017/050701, dated Aug. 30, 2017 (16 pages).

International Search Report and Written Opinion for International Application No. PCT/CA2017/051368, dated Feb. 7, 2018 (11 pages).

International Search Report and Written Opinion for International Application No. PCT/CA2018/051595, dated Aug. 15, 2019 (11 pages).

International Search Report for International Application No. PCT/US2011/049905, dated May 1, 2012 (4 pages).

(56) References Cited

OTHER PUBLICATIONS

Inubushi et al., "Palovarotene Inhibits Osteochondroma Formation in a Mouse Model of Multiple Hereditary Exostoses," J Bone Miner Res. 33(4):658-66 (epub—2017) (9 pages).

Iwamoto et al., "Retinoic acid induces rapid mineralization and expression of mineralization-related genes in chondrocytes," Exp Cell Res 207(2): 413-420 (1993).

Japanese Office Action with English translation for Japanese Patent Application No. 2013- 527250, dated Jul. 30, 2015 (6 pages).

Juurikivi et al., "Inhibition of c-kit tyrosine kinase by imatinib mesylate induces apoptosis in mast cells in rheumatoid synovia: a potential approach to the treatment of arthritis," Ann Rheum Dis. 64(8):1126-31 (2005).

Kaplan et al., "Derailing heterotopic ossification and RARing to go," Nat Med. 17(4):420-421 (2011).

Kaplan et al., "Early clinical observations on the use of imatinib mesylate in FOP: a report of seven cases," Bone. 109, doi: 10.1016/j.bone.2017.07.019 (2017) (Author manuscript) (30 pages).

Kennedy et al., "Retinoic acid enhances skeletal muscle progenitor formation and bypasses inhibition by bone morphogenetic protein 4 but not dominant negative beta-catenin," BMC Biol. 7:67 (2009). (21 pages).

Koyama et al., "Retinoid signaling is required for chondrocyte maturation and endochondral bone formation during limb skeletogenesis," Dev Biol. 208(2):375-91 (1999).

Krueger C et al., "Identification of Retinoic Acid in a High Content Screen for Agents that Overcome the Anti-Myogenic Effect of TGF-Beta-1," PLoS ONE 5(11): e15511 (2010) (11 pages).

Le May et al., Retinoid X Receptor Signalling in the Specification of Skeletal Muscle Lineage. Skeletal Muscle—From Myogenesis to Clinical Relations. Juliana Cseri, 49-72 (2012).

Matsumoto et al., "Conditional ablation of the heparan sulfate-synthesizing enzyme EXT1 leads to dysregulation of bone morphogenic protein signaling and severe skeletal defects," J Biol Chem. 285(25):19227-34 (2010).

Neuville et al., "Retinoic acid regulates arterial smooth muscle cell proliferation and phenotypic features in vivo and in vitro through an RARa-dependent signaling pathway," Arterioscler Thromb Vasc Biol. 19:1430-6 (1999).

Office Action and English Comments for Mexican Patent Application No. MX/a/2013/002275, dated Jan. 12, 2018 (7 pages).

Office Action and English Comments for Mexican Patent Application No. MX/a/2013/002275, dated Jan. 12, 2016 (8 pages).

Office Action and English Comments for Thai Patent Application No. 1301001049, dated Jul. 1, 2015 (5 pages).

Office Action and its English translation for Chinese Patent Application No. 201180052926.X, dated May 8, 2014 (19 pages).

Office Action for Canadian Patent Application No. 2809374, dated Dec. 1, 2017 (4 pages).

Office Action for U.S. Appl. No. 14/308,570, dated Jul. 31, 2014 (7 pages).

Pacifici et al., "Vitamin A inhibits chondrogenesis but not myogenesis," Exp Cell Res. 129(2):469- 74 (1980) (Abstract Only) (1 page).

Pacifici et al., Annual Report for U.S. Army Medical Research and Material Command, Oct. 2014, "Preventative Therapeutics for Heterotopic Ossification," (13 pages).

Pakala et al., "RAR gamma agonists inhibit proliferation of vascular smooth muscle cells," J Cardiovasc Pharmacol. 35(2):302-8 (2000) (Author Manuscript) (17 pages).

Patent Examination Report No. 1 for New Zealand Patent Application No. 607547, dated Oct. 21, 2013 (3 pages).

Patent Examination Report No. 1 in Australian Patent Application No. 2011296080, dated Jul. 4, 2014 (4 pages).

Ray et al., "Signaling of c-kit in dendritic cells influences adaptive immunity," available in PMC May 2, 2013, published in final edited form as: Ann N Y Acad Sci. 1183:104-22 (2010) (23 pages).

Rochette-Egly et al., "Dynamic and combinatorial control of gene expression by nuclear retinoic acid receptors (RARs)," Nuclear Receptor Signaling. 7:1-18 (2009).

Sanvitale et al., "A new class of small molecule inhibitor of BMP signaling," PLoS One. 8(4):e62721 (2013) (11 pages).

Schmale et al., "The natural history of hereditary multiple exostoses," J Bone Joint Surg Am. 76(7):986-92 (1994).

Schneider et al., "Activation of retinoic acid receptor alpha is sufficient for full induction of retinoid responses in SK-BR-3 and T47D human breast cancer cells," Cancer Res. 60(19):5479-87 (2000).

Seale et al., "The potential of muscle stem cells," Dev Cell. 1(3):333-42 (2001).

Second Office Action and English Comments for Chinese Patent Application No. 201180052926.X, dated Mar. 27, 2015 (12 pages).

Shimono et al., "A retinoid composition for rapid muscle repair and regeneration." Poster presented at BioTech 2010 Conference (Oct. 27, 2010).

Shimono et al., "Inhibition of ectopic bone formation by a selective retinoic acid receptor alpha-agonist: A new therapy for heterotopic ossification'?," J Orthop Res. 28(2): 271-277 (2010).

Shimono et al., "Potent inhibition of heterotopic ossification by nuclear retinoic acid receptor-gamma agonists," Nat Med. 17(4):454-60 (2011).

Shiota et al., "The anti-allergic compound tranilast attenuates inflammation and inhibits bone destruction in collagen-induced arthritis in mice," Br J Pharmacol. 159(3):626-35 (2010).

Sinha et al., "Effectiveness and mode of action of a combination therapy for heterotopic ossification with a retinoid agonist and an anti-inflammatory agent," available in PMC Sep. 1, 2017, published in final edited form as: Bone. 90:59-68 (2016) (23 pages).

Sinha et al., "Unsuspected osteochondroma-like outgrowths in the cranial base of Hereditary Multiple Exostoses patients and modeling and treatment with a BMP antagonist in mice," PLoS Genet. 13(4):e1006742 (2017) (26 pages).

Soprano et al., "Role of retinoic acid in the differentiation of embryonal carcinoma and embryonic stem cells." Vitam horm. 75:69-95 (2007).

Supplemental Figure S4 from Di Rocco et al., "Selective retinoic acid receptor gamma agonists promote repair of injured skeletal muscle in mouse," Am J Pathol. 185(9):2495-504 (2015) (2 pages).

Thacher et al., "Therapeutic applications for ligands of retinoid receptors," Curr Pharm Des. 6(1):25-58 (2000).

Third Office Action and English Comments for Chinese Patent Application No. 201180052926.X, dated Oct. 12, 2015 (11 pages).

Wang et al., "Bone Morphogenetic Protein (BMP) signaling in development and human diseases," Genes Dis. 1(1):87-105 (2014).

Wang et al., "Cellular Hypoxia Promotes Heterotopic Ossification by Amplifying BMP Signaling," J Bone Miner Res. 31(9):1652-65 (2016).

Weston et al., "Requirement for RAR-mediated gene repression in skeletal progenitor differentiation," J Cell Biol. 158(1):39-51 (2002).

Weston et al., "Revisiting the role of retinoid signaling in skeletal development," Birth Defects Res C Embryo Today. 69(2):156-73 (2003).

Williams et al., "Retinoic acid receptors are required for skeletal growth, matrix homeostasis and growth plate function in postnatal mouse," Dev Biol. 328(2):315-27 (2009).

Wozney et al., "Novel regulators of bone formation: molecular clones and activities," Science. 242(4885):1528-34 (1988).

Wuyts et al., "Hereditary Multiple Osteochondromas," GeneReviews, posted Aug. 3, 2000, last updated Nov. 21, 2013 (17 pages).

Yasuhara et al. "Wnt/beta-catenin and retinoic acid receptor signaling pathways interact to regulate chondrocyte function and matrix turnover." J Biol Chem. 285(1):317-327 (2010).

Yu et al., "BMP type I receptor inhibition reduces heterotopic [corrected] ossification," available in PMC Mar. 29, 2010, published in final edited form as: Nat Med. 14(12):1363-9 (2008) (14 pages).

Zasloff et al., "Treatment of patients who have fibrodysplasia ossificans progressiva with isotretinoin," Clin Orthop Relat Res. 346:121-9 (1998).

International Search Report and Written Opinion for International Application No. PCT/CA2019/051803, dated Feb. 20, 2020 (10 pages).

(56) References Cited

OTHER PUBLICATIONS

Jones et al., "TESRA (Treatment of Emphysema With a Selective Retinoid Agonist) Study Results," Am J Respir Crit Care Med. 183:A6418 (2011) (2 pages).

Stolk et al., "Randomised controlled trial for emphysema with a selective agonist of the gamma-type retinoic acid receptor," Eur Respir J. 40(2):306-12 (2012).

* cited by examiner

METHODS FOR TREATING HETEROTOPIC OSSIFICATION

RELATED APPLICATIONS

The present Patent Cooperation Treaty application claims priority to U.S. application No. 62/347,381 filed on Jun. 8, 2016, which is herein incorporated by reference in its entirety.

BACKGROUND OF THE INVENTION

Some patients with fibrodysplasia ossificans progressiva (FOP) experience muscle, tendon, and/or ligament damage, e.g., soft tissue edema and muscle necrosis, especially concomitant with flare-up symptom onset. These spontaneous muscle, tendon, and/or ligament injuries, and those due to trauma, can lead to heterotopic ossification, can cause tremendous pain, and can incapacitate the affected person. There are no currently approved treatments for muscle, tendon, and/or ligament injury in FOP subjects that prevent heterotopic ossification.

SUMMARY OF THE INVENTION

The invention features dosing regimens and pharmaceutical formulations for oral administration of palovarotene.

The invention features a method of reducing heterotopic ossification in a subject with fibrodysplasia ossificans progressiva (also known as myositis ossificans progressive, a disease characterized by damage to muscle tissue) characterized by a quiescent period and a non-quiescent period, the method including: (i) during the quiescent period administering daily to the subject an amount of 3±2 mg of palovarotene, or a pharmaceutically acceptable salt thereof, and (ii) during the non-quiescent period administering daily to the subject 2-fold to 6-fold the amount administered daily during the quiescent period. In particular embodiments, during the non-quiescent period palovarotene, or a pharmaceutically acceptable salt thereof, is initially administered in a daily loading dose of 3.5-fold to 6-fold the amount administered daily during the quiescent period followed by a daily maintenance dose of 2-fold to 3-fold the amount administered daily during the quiescent period. For example, the amount administered during the quiescent period can be 3±0.5 mg daily and the amount administered during the non-quiescent period can include a daily loading dose of 12.5±1.0 mg daily and a daily maintenance dose of 6.0±1.0 mg daily. Optionally, for this dosing regimen the subject weighs from 20 to 40 kg. In another example, the amount administered during the quiescent period can be 4±0.5 mg daily and the amount administered during the non-quiescent period can include a daily loading dose of 15±1.0 mg daily and a daily maintenance dose of 7.5±1.0 mg daily. Optionally, for this dosing regimen the subject weighs from 40 to 60 kg. In still another example, the amount administered during the quiescent period can be 5±0.5 mg daily and the amount administered during the non-quiescent period can include a daily loading dose of 20±1.0 mg daily and a daily maintenance dose of 10±1.0 mg daily. Optionally, for this dosing regimen the subject weighs greater than 60 kg. In some embodiments, the amount administered during the quiescent period is 2±0.5 mg daily and the amount administered during the non-quiescent period comprises a daily loading dose of 10±1.0 mg daily and a daily maintenance dose of 5±1.0 mg daily. Optionally, for this dosing regimen the subject weighs less than 20 kg. In any of the above methods, the daily loading dose is administered for a period of 20 to 40 days (e.g., 24±4 days, 28±4 days, 32±4 days, 36±4 days, or 20, 21, 22, 23, 24, 25, 26, 27, 28, 29, 30, 31, 32, 33, 34, 35, 36, 37, 38, 39 or 40 days). In particular embodiments, the daily maintenance dose is administered for at least a period of 14 to 84 days (e.g., 21±7 days, 28±14 days, 42±14 days, 63±14 days, 72±12 days, or 52, 53, 54, 55, 56, 57, 58, 58, 60, or 84 days). Optionally, at the end of 84 days the daily maintenance dose is continued for an additional 28 days (i.e., a total of 112 days) if the subject continues to experience flare-ups or flare-up symptoms, or the maintenance dose regimen is continued until the flare-ups or flare-up symptoms subside or cease. In particular embodiments, at the end of 112 days the daily maintenance dose is continued for an additional 28 days (i.e., a total of 140 days) if the subject continues to experience flare-ups or flare-up symptoms, or the maintenance dose regimen is continued until the flare-ups or flare-up symptoms subside or cease. In some embodiments, a daily loading dose of 20 mg is administered for 28 days, a daily maintenance dose of 10 mg is administered for 56 days and the amount administered during the quiescent period is 5 mg/day. In some embodiments, a daily loading dose of 15 mg is administered for 28 days and a daily maintenance dose of 10 mg is administered for 56 days and the amount administered during the quiescent period is 5 mg/day. Once the non-quiescent period has resolved, the subject can return to the lower level quiescent period dosing regimen.

In one embodiment, the invention features a method of reducing heterotopic ossification in a subject with fibrodysplasia ossificans progressiva characterized by quiescent periods and non-quiescent periods, the method including: (i) administering 3.0+/−2.0 mg/day palovarotene, or a pharmaceutically acceptable salt thereof, during quiescent periods, and (ii) administering an amount between 10 mg/day palovarotene, or a pharmaceutically acceptable salt thereof, and 20 mg/day palovarotene, or a pharmaceutically acceptable salt thereof, for from 84 to 140 days following the start of a non-quiescent period.

In one embodiment, the invention features a method of reducing heterotopic ossification in a subject with fibrodysplasia ossificans progressiva characterized by quiescent periods and non-quiescent periods, the method including: (i) administering 5 mg/day palovarotene, or a pharmaceutically acceptable salt thereof, during quiescent periods, and (ii) administering 20 mg/day palovarotene, or a pharmaceutically acceptable salt thereof, for 28 days followed by 10 mg/day palovarotene, or a pharmaceutically acceptable salt thereof, for 56 days following the start of a non-quiescent period. In a further embodiment, the invention features a method of reducing heterotopic ossification in a subject with fibrodysplasia ossificans progressiva characterized by quiescent periods and non-quiescent periods, the method including: (i) administering 5 mg/day palovarotene, or a pharmaceutically acceptable salt thereof, during quiescent periods, and (ii) administering 20 mg/day palovarotene, or a pharmaceutically acceptable salt thereof, for 28 days followed by 10 mg/day palovarotene, or a pharmaceutically acceptable salt thereof, for 84 days following the start of a non-quiescent period. In yet a further embodiment, the invention features a method of reducing heterotopic ossification in a subject with fibrodysplasia ossificans progressiva characterized by quiescent periods and non-quiescent periods, the method including: (i) administering 5 mg/day palovarotene, or a pharmaceutically acceptable salt thereof, during quiescent periods, and (ii) administering 20 mg/day palovarotene, or a pharmaceutically acceptable salt thereof, for 28 days followed by 10 mg/day palovarotene, or a pharmaceutically acceptable salt thereof, for 112 days following the start of a non-quiescent period.

The invention features a method of reducing heterotopic ossification in a subject with fibrodysplasia ossificans progressiva characterized by a quiescent period and a non-quiescent period, the method including during the non-quiescent period: (i) administering to the subject a loading dose in an amount of from 9 to 21 mg of palovarotene, or a pharmaceutically acceptable salt thereof, daily during a first time period and (ii) following the first time period, administering daily to the subject a maintenance dose of 40% to 60% of the amount administered in the loading dose. In some embodiments, the daily loading dose is 12.5±1.0 mg daily and the maintenance dose is 6.0±1.0 mg daily. Optionally, the subject weighs from 20 to 40 kg. In still other embodiments, the loading dose is 15±1.0 mg daily and the maintenance dose of 7.5±1.0 mg daily. Optionally, the subject weighs from 40 to 60 kg. In certain embodiments, the method of claim 39, wherein the loading dose is 20±1.0 mg daily and the maintenance dose of 10±1.0 mg daily. Optionally, the subject weighs greater than 60 kg. In any of the above methods, the loading dose is administered for a period of 20 to 40 days (e.g., 24±4 days, 28±4, days, 32±4 days, or 36±4 days, or 20, 21, 22, 23, 24, 25, 26, 27, 28, 29, 30, 31, 32, 33, 34, 35, 36, 37, 38, 39 or 40 days). In particular embodiments, the maintenance dose is administered for at least a period of 14 to 84 days (e.g., 21±7 days, 28±14 days, 42±14 days, 63±14 days, 72±12 days, or 52, 53, 54, 55, 56, 57, 58, 58, 60, or 84 days). Optionally, at the end of 84 days the maintenance dose is continued for an additional 28 days (i.e., a total of 112 days) if the subject continues to experience flare-ups or flare-up symptoms, or the maintenance dose regimen is continued until the flare-ups or flare-up symptoms subside or cease. In particular embodiments, at the end of 112 days the daily maintenance dose is continued for an additional 28 days (i.e., a total of 140 days) if the subject continues to experience flare-ups or flare-up symptoms, or the maintenance dose regimen is continued until the flare-ups or flare-up symptoms subside or cease.

The invention features a method of reducing the severity of flare-ups or flare-up symptoms in a subject with fibrodysplasia ossificans progressiva characterized by a quiescent period and a non-quiescent period, the method including: (i) during the quiescent period administering daily to the subject an amount of 3±2 mg of palovarotene, or a pharmaceutically acceptable salt thereof, and (ii) during the non-quiescent period administering daily to the subject 2-fold to 6-fold the amount administered daily during the quiescent period. In particular embodiments, during the non-quiescent period the palovarotene, or a pharmaceutically acceptable salt thereof, is initially administered in a daily loading dose of 3.5-fold to 6-fold the amount administered daily during the quiescent period followed by a daily maintenance dose of 2-fold to 3-fold the amount administered daily during the quiescent period. For example, the amount administered during the quiescent period can be 3±0.5 mg daily and the amount administered during the non-quiescent period can include a daily loading dose of 12.5±1.0 mg daily and a daily maintenance dose of 6.0±1.0 mg daily. Optionally, for this dosing regimen the subject weighs from 20 to 40 kg. In another example, the amount administered during the quiescent period can be 4±0.5 mg daily and the amount administered during the non-quiescent period can include a daily loading dose of 15±1.0 mg daily and a daily maintenance dose of 7.5±1.0 mg daily. Optionally, for this dosing regimen the subject weighs from 40 to 60 kg. In still another example, the amount administered during the quiescent period can be 5±0.5 mg daily and the amount administered during the non-quiescent period can include a daily loading dose of 20±1.0 mg daily and a daily maintenance dose of 10±1.0 mg daily. Optionally, for this dosing regimen the subject weighs greater than 60 kg. In some embodiments, the amount administered during the quiescent period is 2±0.5 mg daily and the amount administered during the non-quiescent period comprises a daily loading dose of 10±1.0 mg daily and a daily maintenance dose of 5±1.0 mg daily. Optionally, for this dosing regimen the subject weighs less than 20 kg. In any of the above methods, the daily loading dose is administered for a period of 20 to 40 days (e.g., 24±4 days, 28±4 days, 32±4 days, or 36±4 days). In particular embodiments, the daily maintenance dose is administered for at least a period of 14 to 84 days (e.g., 21±7 days, 28±14 days, 42±14 days, 63±14 days, or 72±12 days). Optionally, at the end of 84 days the daily maintenance dose is continued for an additional 28 days if the subject continues to experience flare-ups or flare-up symptoms, or the maintenance dose regimen is continued until the flare-ups or flare-up symptoms subside or cease. In particular embodiments of the method the number of flare-ups is reduced in a subject or the frequency of flare-ups is reduced in a subject. Once the non-quiescent period has resolved, the subject can return to the lower level quiescent period dosing regimen.

In one embodiment, the invention features a method of reducing the severity of flare-ups or flare-up symptoms in a subject with fibrodysplasia ossificans progressiva characterized by quiescent periods and non-quiescent periods, the method including: (i) administering 3.0+/−2.0 mg/day palovarotene, or a pharmaceutically acceptable salt thereof, during quiescent periods, and (ii) administering an amount between 10 mg/day palovarotene, or a pharmaceutically acceptable salt thereof, and 20 mg/day palovarotene, or a pharmaceutically acceptable salt thereof, for from 84 to 140 days following the start of a non-quiescent period.

The invention features a method of reducing the flare-up rate in a subject with fibrodysplasia ossificans progressiva characterized by a quiescent period and a non-quiescent period, the method including: (i) during the quiescent period administering daily to the subject an amount of 3±2 mg of palovarotene, or a pharmaceutically acceptable salt thereof, and (ii) during the non-quiescent period administering daily to the subject 2-fold to 6-fold the amount administered daily during the quiescent period. In particular embodiments, during the non-quiescent period palovarotene, or a pharmaceutically acceptable salt thereof, is initially administered in a daily loading dose of 3.5-fold to 6-fold the amount administered daily during the quiescent period followed by a daily maintenance dose of 2-fold to 3-fold the amount administered daily during the quiescent period. For example, the amount administered during the quiescent period can be 3±0.5 mg daily and the amount administered during the non-quiescent period can include a daily loading dose of 12.5±1.0 mg daily and a daily maintenance dose of 6.0±1.0 mg daily. Optionally, for this dosing regimen the subject weighs from 20 to 40 kg. In another example, the amount administered during the quiescent period can be 4±0.5 mg daily and the amount administered during the non-quiescent period can include a daily loading dose of 15±1.0 mg daily and a daily maintenance dose of 7.5±1.0 mg daily. Optionally, for this dosing regimen the subject weighs from 40 to 60 kg. In still another example, the amount administered during the quiescent period can be 5±0.5 mg daily and the amount administered during the non-quiescent period can include a daily loading dose of 20±1.0 mg daily and a daily maintenance dose of 10±1.0 mg daily. Optionally, for this dosing regimen the subject weighs greater than 60 kg. In some embodiments, the amount administered during the quiescent period is 2±0.5 mg daily and the amount administered during the non-quiescent period comprises a daily loading dose of 10±1.0 mg daily and a daily maintenance dose of 5±1.0 mg daily. Optionally, for this dosing regimen the subject weighs less than 20 kg. In any of the above methods, the daily loading dose is administered for a period of 20 to 40 days (e.g., 24±4 days, 28±4 days, 32±4 days, or 36±4 days). In particular embodiments, the daily maintenance dose is administered for at least a period of 14 to 84 days (e.g., 21±7 days, 28±14 days, 42±14 days, 63±14 days, or 72±12 days). Optionally, at the end of 84 days the daily maintenance dose is continued for an additional 28 days if the subject continues to experience flare-ups or flare-up symptoms, or the maintenance dose regimen is continued until the flare-ups or flare-up symptoms subside or cease. In particular embodiments of the method, the number of flare-ups is reduced in a subject or the frequency of flare-ups is reduced in a subject. Once the non-quiescent period has resolved, the subject can return to the lower level quiescent period dosing regimen.

The invention features a method of reducing heterotopic ossification in a subject with fibrodysplasia ossificans progressiva characterized by a quiescent period and a non-quiescent period, said method comprising: (i) during the quiescent period administering daily to the subject a first amount of a BMP signaling inhibitor and (ii) during the non-quiescent period administering daily to the subject 2-fold to 6-fold the amount administered daily during the quiescent period. In some embodiments of this method, during the non-quiescent period the BMP signaling inhibitor, is initially administered in a daily loading dose of 3.5-fold to 6-fold the amount administered daily during the quiescent period followed by a daily maintenance dose of 2-fold to 3-fold the amount administered daily during the quiescent period. In some embodiments, the BMP signaling inhibitor is an activin receptor-like 2 (ALK2) kinase inhibitor. In particular, the ALK2 kinase inhibitor is LDN-193189 (4-(6-(4-(piperazin-1-yl)phenyl)pyrazolo[1,5-a]pyrimidin-3-yl)-quinolone), LDN-212854 (5-[6-[4-(1-piperazinyl)phenyl]pyrazolo[1,5-a]pyrimidin-3-yl]-quinoline), dorsomorphin (6-[4-[2-(1-Piperidinyl)ethoxy]phenyl]-3-(4-pyridinyl)-pyrazolo[1,5-a]-pyrimidine), K02288 (3-[(6-Amino-5-(3,4,5-trimethoxyphenyl)-3-pyridinyl]-phenol), DMH-1 (4-[6-[4-(1-Methylethoxy)phenyl]pyrazolo[1,5-a]pyrimidin-3-yl]-quinoline), or ML-347 (5-[6-(4-Methoxyphenyl)pyrazolo[1,5-a]pyrimidin-3-yl]-quinolone).

The invention features a method of reducing heterotopic ossification in a subject with fibrodysplasia ossificans progressiva characterized by a quiescent period and a non-quiescent period, the method including: (i) during the quiescent period administering daily to the subject an amount of 5 mg of palovarotene, or a pharmaceutically acceptable salt thereof, and (ii) during the non-quiescent period administering daily to the subject 20 mg of palovarotene, or a pharmaceutically acceptable salt thereof, for 28 days, followed by administering daily to the subject 10 mg of palovarotene, or a pharmaceutically acceptable salt thereof, for at least 56 days. Optionally, at the end of 56 days the daily 10 mg dose is continued for an additional 28 days (i.e., a total of 84 days) if the subject continues to experience flare-ups or flare-up symptoms, or the 10 mg dose regimen is continued until the flare-ups or flare-up symptoms subside or cease. In some embodiments, at the end of 84 days the daily 10 mg dose is continued for an additional 28 days (i.e., a total of 112 days) if the subject continues to experience flare-ups or flare-up symptoms, or the 10 mg dose regimen is continued until the flare-ups or flare-up symptoms subside or cease. In particular embodiments, at the end of 112 days the daily 10 mg dose is continued for an additional 28 days (i.e., a total of 140 days) if the subject continues to experience flare-ups or flare-up symptoms, or the 10 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, wherein the subject weighs from 10 to 20 kg, the method including: (i) during the quiescent period administering daily to the subject an amount of 2.5 mg of palovarotene, or a pharmaceutically acceptable salt thereof, and (ii) during the non-quiescent period administering daily to the subject 10 mg of palovarotene, or a pharmaceutically acceptable salt thereof, for 28 days, followed by administering daily to the subject 5 mg of palovarotene, or a pharmaceutically acceptable salt thereof, for at least 56 days. Optionally, at the end of 56 days the daily 5 mg dose is continued for an additional 28 days (i.e., a total of 84 days) if the subject continues to experience flare-ups or flare-up symptoms, or the 5 mg dose regimen is continued until the flare-ups or flare-up symptoms subside or cease. In some embodiments, at the end of 84 days the daily 5 mg dose is continued for an additional 28 days (i.e., a total of 112 days) if the subject continues to experience flare-ups or flare-up symptoms, or the 5 mg dose regimen is continued until the flare-ups or flare-up symptoms subside or cease. In particular embodiments, at the end of 112 days the daily 5 mg dose is continued for an additional 28 days (i.e., a total of 140 days) if the subject continues to experience flare-ups or flare-up symptoms, or the 5 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, wherein the subject weighs from 20 to 40 kg, the method including: (i) during the quiescent period administering daily to the subject an amount of 3 mg of palovarotene, or a pharmaceutically acceptable salt thereof, and (ii) during the non-quiescent period administering daily to the subject 12.5 mg of palovarotene, or a pharmaceutically acceptable salt thereof, for 28 days, followed by administering daily to the subject 6 mg of palovarotene, or a pharmaceutically acceptable salt thereof, for at least 56 days. Optionally, at the end of 56 days the daily 6 mg dose is continued for an additional 28 days (i.e., a total of 84 days) if the subject continues to experience flare-ups or flare-up symptoms, or the 6 mg dose regimen is continued until the flare-ups or flare-up symptoms subside or cease. In some embodiments, at the end of 84 days the daily 6 mg dose is continued for an additional 28 days (i.e., a total of 112 days) if the subject continues to experience flare-ups or flare-up symptoms, or the 6 mg dose regimen is continued until the flare-ups or flare-up symptoms subside or cease. In particular embodiments, at the end of 112 days the daily 6 mg dose is continued for an additional 28 days (i.e., a total of 140 days) if the subject continues to experience flare-ups or flare-up symptoms, or the 6 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, wherein the subject weighs from 40 to 60 kg, the method including: (i) during the quiescent period administering daily to the subject an amount of 4 mg of palovarotene, or a pharmaceutically acceptable salt thereof, and (ii) during the non-quiescent period administering daily to the subject 15 mg of palovarotene, or a pharmaceutically acceptable salt thereof, for 28 days, followed by administering daily to the subject 7.5 mg of palovarotene, or a pharmaceutically acceptable salt thereof, for at least 56 days. Optionally, at the end of 56 days the daily 7.5 mg dose is continued for an additional 28 days (i.e., a total of 84 days) if the subject continues to experience flare-ups or flare-up symptoms, or the 7.5 mg dose regimen is continued until the flare-ups or flare-up symptoms subside or cease. In some embodiments, at the end of 84 days the daily 7.5 mg dose is continued for an additional 28 days (i.e., a total of 112 days) if the subject continues to experience flare-ups or flare-up symptoms, or the 7.5 mg dose regimen is continued until the flare-ups or flare-up symptoms subside or cease. In particular embodiments, at the end of 112 days the daily 7.5 mg dose is continued for an additional 28 days (i.e., a total of 140 days) if the subject continues to experience flare-ups or flare-up symptoms, or the 7.5 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, wherein the subject weighs 60 kg or more, the method including: (i) during the quiescent period administering daily to the subject an amount of 5 mg of palovarotene, or a pharmaceutically acceptable salt thereof, and (ii) during the non-quiescent period administering daily to the subject 20 mg of palovarotene, or a pharmaceutically acceptable salt thereof, for 28 days, followed by administering daily to the subject 10 mg of palovarotene, or a pharmaceutically acceptable salt thereof, for at least 56 days. Optionally, at the end of 56 days the daily 10 mg dose is continued for an additional 28 days (i.e., a total of 84 days) if the subject continues to experience flare-ups or flare-up symptoms, or the 10 mg dose regimen is continued until the flare-ups or flare-up symptoms subside or cease. In some embodiments, at the end of 84 days the daily 10 mg dose is continued for an additional 28 days (i.e., a total of 112 days) if the subject continues to experience flare-ups or flare-up symptoms, or the 10 mg dose regimen is continued until the flare-ups or flare-up symptoms subside or cease. In particular embodiments, at the end of 112 days the daily 10 mg dose is continued for an additional 28 days (i.e., a total of 140 days) if the subject continues to experience flare-ups or flare-up symptoms, or the 10 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, the method including: (i) during the quiescent period administering daily to the subject an amount of 4 mg of palovarotene, or a pharmaceutically acceptable salt thereof, and (ii) during the non-quiescent period administering daily to the subject 15 mg of palovarotene, or a pharmaceutically acceptable salt thereof, for 28 days, followed by administering daily to the subject 7.5 mg of palovarotene, or a pharmaceutically acceptable salt thereof, for at least 56 days. Optionally, at the end of 56 days the daily 7.5 mg dose is continued for an additional 28 days (i.e., a total of 84 days) if the subject continues to experience flare-ups or flare-up symptoms, or the 7.5 mg dose regimen is continued until the flare-ups or flare-up symptoms subside or cease. In some embodiments, at the end of 84 days the daily 7.5 mg dose is continued for an additional 28 days (i.e., a total of 112 days) if the subject continues to experience flare-ups or flare-up symptoms, or the 7.5 mg dose regimen is continued until the flare-ups or flare-up symptoms subside or cease. In particular embodiments, at the end of 112 days the daily 7.5 mg dose is continued for an additional 28 days (i.e., a total of 140 days) if the subject continues to experience flare-ups or flare-up symptoms, or the 7.5 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, wherein the subject weighs from 10 to 20 kg, the method including: (i) during the quiescent period administering daily to the subject an amount of 1 mg of palovarotene, or a pharmaceutically acceptable salt thereof, and (ii) during the non-quiescent period administering daily to the subject 7.5 mg of palovarotene, or a pharmaceutically acceptable salt thereof, for 28 days, followed by administering daily to the subject 3 mg of palovarotene, or a pharmaceutically acceptable salt thereof, for at least 56 days. Optionally, at the end of 56 days the daily 3 mg dose is continued for an additional 28 days (i.e., a total of 84 days) if the subject continues to experience flare-ups or flare-up symptoms, or the 3 mg dose regimen is continued until the flare-ups or flare-up symptoms subside or cease. In some embodiments, at the end of 84 days the daily 3 mg dose is continued for an additional 28 days (i.e., a total of 112 days) if the subject continues to experience flare-ups or flare-up symptoms, or the 3 mg dose regimen is continued until the flare-ups or flare-up symptoms subside or cease. In particular embodiments, at the end of 112 days the daily 3 mg dose is continued for an additional 28 days (i.e., a total of 140 days) if the subject continues to experience flare-ups or flare-up symptoms, or the 3 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, wherein the subject weighs from 20 to 40 kg, the method including: (i) during the quiescent period administering daily to the subject an amount of 2.5 mg of palovarotene, or a pharmaceutically acceptable salt thereof, and (ii) during the non-quiescent period administering daily to the subject 10 mg of palovarotene, or a pharmaceutically acceptable salt thereof, for 28 days, followed by administering daily to the subject 5 mg of palovarotene, or a pharmaceutically acceptable salt thereof, for at least 56 days. Optionally, at the end of 56 days the daily 5 mg dose is continued for an additional 28 days (i.e., a total of 84 days) if the subject continues to experience flare-ups or flare-up symptoms, or the 5 mg dose regimen is continued until the flare-ups or flare-up symptoms subside or cease. In some embodiments, at the end of 84 days the daily 5 mg dose is continued for an additional 28 days (i.e., a total of 112 days) if the subject continues to experience flare-ups or flare-up symptoms, or the 5 mg dose regimen is continued until the flare-ups or flare-up symptoms subside or cease. In particular embodiments, at the end of 112 days the daily 5 mg dose is continued for an additional 28 days (i.e., a total of 140 days) if the subject continues to experience flare-ups or flare-up symptoms, or the 5 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, wherein the subject weighs from 40 to 60 kg, the method including: (i) during the quiescent period administering daily to the subject an amount of 3 mg of palovarotene, or a pharmaceutically acceptable salt thereof, and (ii) during the non-quiescent period administering daily to the subject 12.5 mg of palovarotene, or a pharmaceutically acceptable salt thereof, for 28 days, followed by administering daily to the subject 6 mg of palovarotene, or a pharmaceutically acceptable salt thereof, for at least 56 days. Optionally, at the end of 56 days the daily maintenance dose is continued for an additional 28 days (i.e., a total of 84 days) if the subject continues to experience flare-ups or flare-up symptoms, or the 6 mg dose regimen is continued until the flare-ups or flare-up symptoms subside or cease. In some embodiments, at the end of 84 days the daily 6 mg dose is continued for an additional 28 days (i.e., a total of 112 days) if the subject continues to experience flare-ups or flare-up symptoms, or the 6 mg dose regimen is continued until the flare-ups or flare-up symptoms subside or cease. In particular embodiments, at the end of 112 days the daily 6 mg dose is continued for an additional 28 days (i.e., a total of 140 days) if the subject continues to experience flare-ups or flare-up symptoms, or the 6 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, wherein the subject weighs 60 kg or more, the method including: (i) during the quiescent period administering daily to the subject an amount of 4 mg of palovarotene, or a pharmaceutically acceptable salt thereof, and (ii) during the non-quiescent period administering daily to the subject 15 mg of palovarotene, or a pharmaceutically acceptable salt thereof, for 28 days, followed by administering daily to the subject 7.5 mg of palovarotene, or a pharmaceutically acceptable salt thereof, for at least 56 days. Optionally, at the end of 56 days the daily 7.5 mg dose is continued for an additional 28 days (i.e., a total of 84 days) if the subject continues to experience flare-ups or flare-up symptoms, or the 7.5 mg dose regimen is continued until the flare-ups or flare-up symptoms subside or cease. In some embodiments, at the end of 84 days the daily 7.5 mg dose is continued for an additional 28 days (i.e., a total of 112 days) if the subject continues to experience flare-ups or flare-up symptoms, or the 7.5 mg dose regimen is continued until the flare-ups or flare-up symptoms subside or cease. In particular embodiments, at the end of 112 days the daily 7.5 mg dose is continued for an additional 28 days (i.e., a total of 140 days) if the subject continues to experience flare-ups or flare-up symptoms, or the 7.5 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, the method including: (i) during the quiescent period administering daily to the subject an amount of 5 mg of palovarotene, or a pharmaceutically acceptable salt thereof, and (ii) during the non-quiescent period administering daily to the subject 10 mg of palovarotene, or a pharmaceutically acceptable salt thereof, for at least 56 days. Optionally, at the end of 56 days the 10 mg daily dose is continued for an additional 28 days (i.e., a total of 84 days) if the subject continues to experience flare-ups or flare-up symptoms, or the 10 mg dose regimen is continued until the flare-ups or flare-up symptoms subside or cease. In some embodiments, at the end of 84 days the daily 10 mg dose is continued for an additional 28 days (i.e., a total of 112 days) if the subject continues to experience flare-ups or flare-up symptoms, or the 10 mg dose regimen is continued until the flare-ups or flare-up symptoms subside or cease. In particular embodiments, at the end of 112 days the daily 10 mg dose is continued for an additional 28 days (i.e., a total of 140 days) if the subject continues to experience flare-ups or flare-up symptoms, or the 10 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, said method including: (i) during the quiescent period administering daily to the subject an amount of 5 mg of palovarotene, or a pharmaceutically acceptable salt thereof, and (ii) during the non-quiescent period administering daily to the subject 15 mg of palovarotene, or a pharmaceutically acceptable salt thereof, for 28 days, followed by administering daily to the subject 10 mg of palovarotene, or a pharmaceutically acceptable salt thereof, for at least 56 days. Optionally, at the end of 56 days the 10 mg daily dose is continued for an additional 28 days (i.e., a total of 84 days) if the subject continues to experience flare-ups or flare-up symptoms, or the 10 mg dose regimen is continued until the flare-ups or flare-up symptoms subside or cease. In some embodiments, at the end of 84 days the daily 10 mg dose is continued for an additional 28 days (i.e., a total of 112 days) if the subject continues to experience flare-ups or flare-up symptoms, or the 10 mg dose regimen is continued until the flare-ups or flare-up symptoms subside or cease. In particular embodiments, at the end of 112 days the daily 10 mg dose is continued for an additional 28 days (i.e., a total of 140 days) if the subject continues to experience flare-ups or flare-up symptoms, or the 10 mg dose regimen is continued until the flare-ups or flare-up symptoms subside or cease.

The invention features a method of reducing heterotopic ossification in a subject with fibrodysplasia ossificans progressiva characterized by a quiescent period and a non-quiescent period, said method comprising: (i) during the quiescent period administering daily to the subject an amount of 5 mg of palovarotene, or a pharmaceutically acceptable salt thereof, and (ii) during the non-quiescent period administering daily to the subject 10 mg of palovarotene, or a pharmaceutically acceptable salt thereof, for 28 days, followed by administering daily to the subject 10 mg of palovarotene, or a pharmaceutically acceptable salt thereof, for at least 56 days. Optionally, at the end of 56 days the 10 mg daily dose is continued for an additional 28 days (i.e., a total of 84 days) if the subject continues to experience flare-ups or flare-up symptoms, or the 10 mg dose regimen is continued until the flare-ups or flare-up symptoms subside or cease. In some embodiments, at the end of 84 days the daily 10 mg dose is continued for an additional 28 days (i.e., a total of 112 days) if the subject continues to experience flare-ups or flare-up symptoms, or the 10 mg dose regimen is continued until the flare-ups or flare-up symptoms subside or cease. In particular embodiments, at the end of 112 days the daily 10 mg dose is continued for an additional 28 days (i.e., a total of 140 days) if the subject continues to experience flare-ups or flare-up symptoms, or the 10 mg dose regimen is continued until the flare-ups or flare-up symptoms subside or cease.

In any of the above methods, the subject can be an adult. Alternatively, the subject can be a child or adolescent who has not achieved 90% skeletal maturity.

In any of the above methods, the method can further include administering to the subject an antihistamine (e.g., topically or systemically).

In any of the above methods, the method can further include administering to the skin of the subject an emollient.

In any of the above methods, the method can further include administering to the subject a corticosteroid, (e.g., topically or systemically).

As used herein, the term "heterotopic ossification" or "HO" refers to the presence of bone in soft tissue where bone normally does not exist. The HO can be caused by fibrodysplasia ossificans progressiva, a rare genetic condition.

As used herein, the term "reducing the flare-up rate" refers to a reduction in the number or frequency of flare-ups in subjects undergoing treatment with palovarotene using the methods described herein in comparison to untreated subjects.

As used herein, the term "quiescent period" refers to time periods during which a subject with FOP is not experiencing a non-quiescent period.

As used herein, the term "non-quiescent period" refers to time periods during which a subject with FOP is experiencing a flare-up or is at risk of heterotopic ossification triggered by a flare-up or surgery.

As used herein, the term "reducing the severity of flare-ups" refers to an average reduction in one or more flare-up symptoms in subjects undergoing treatment with palovarotene using the methods described herein in comparison to untreated subjects.

As used herein, the term "reducing heterotopic ossification" refers to the average reduction in the amount of bone formed, or number of sites at which bone is formed, in soft tissue by subjects undergoing treatment with palovarotene using the methods described herein in comparison to untreated subjects.

As used herein, the term "flare-up" refers to symptoms related to a local inflammation at an anatomical site where HO is initiated. In FOP subjects a local flare-up is characterized by swelling, pain, erythema, warmth, stiffness and decreased range of motion preceding overt bone formation. Such local inflammation, and early stage lesions, can be associated with the presence and accumulation of innate immune cells, including mast cells that are thought to have an important role in inducing and initiating the HO formation process. As a consequence, the current standard of care for FOP patients includes systemic treatment with corticosteroids within 24 hours of the onset of a flare-up, with treatment continued for several days to reduce inflammation and pain. However, corticosteroids have not been shown to reliably prevent HO. Flare-ups are often injury induced and can include, for example, flare-ups following surgery to excise bone from a soft tissue in FOP subject. The methods described herein can be useful for the treatment of FOP following surgery.

DESCRIPTION OF THE DRAWINGS

FIG. 3A displays the three groups with the two "PVO Non-Quiescent Only" doses pooled, and FIG. 3B displays the two "PVO Non-Quiescent Only" doses as separate bars. FIG. 3B shows that doubling the amount of palovarotene administered only during non-quiescent periods had a small effect on the volume of new heterotopic ossification (i.e., 2,672 mm$^3$ versus 2,216 mm$^3$). In contrast, the amount of new heterotopic ossification was dramatically reduced when treatment included the administration of palovarotene during both quiescent and non-quiescent periods (i.e., 212 mm$^3$).

DETAILED DESCRIPTION OF THE INVENTION

Figure 1:
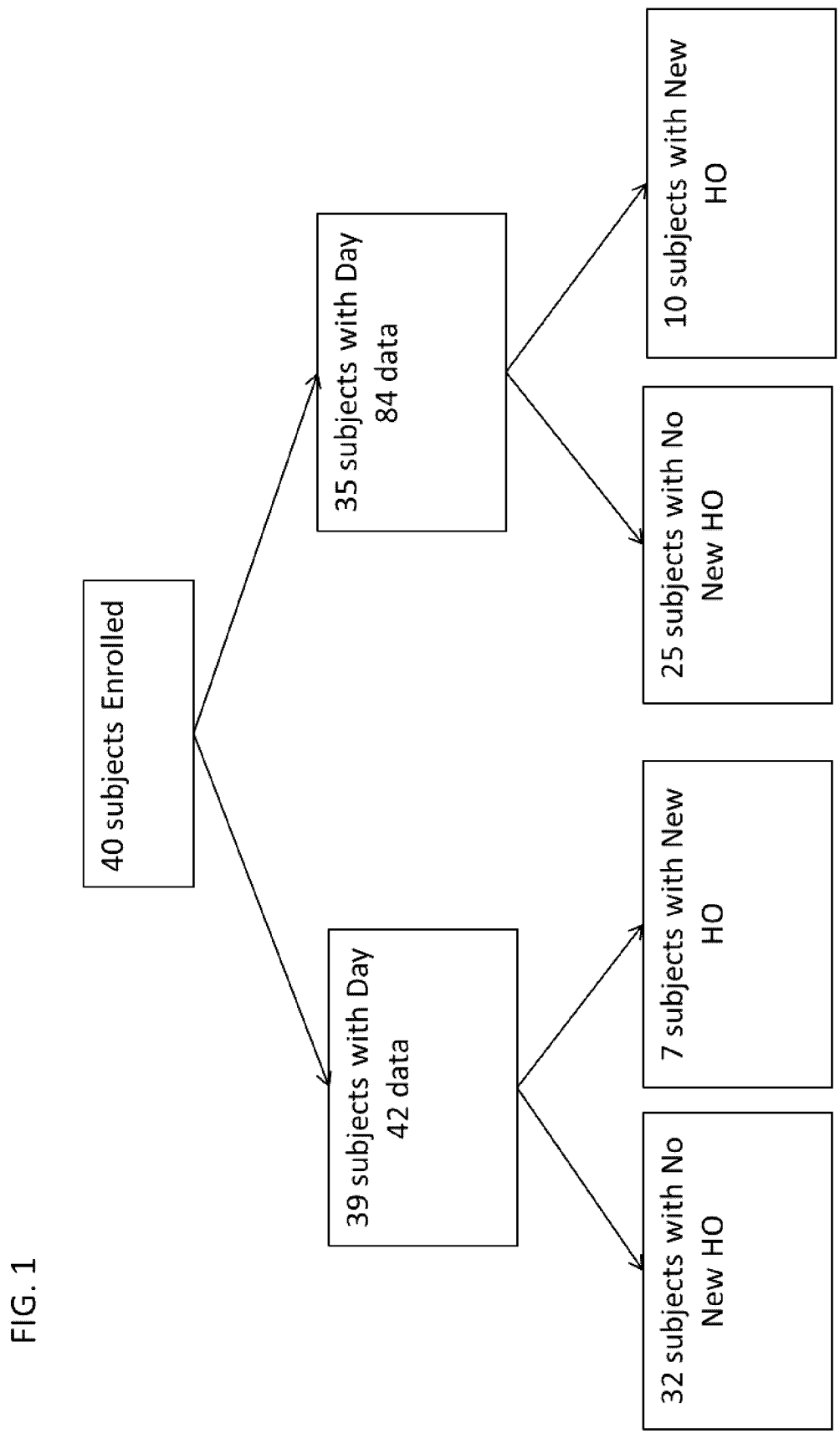
FIG. 1 is a chart displaying flare-up outcomes from double-blind study including 40 subjects.

The invention features dosing regimens and pharmaceutical formulations for oral administration of palovarotene. The dosing regimens can reduce heterotopic ossification, reduce the number of flare-ups, and/or reduce the severity of flare-ups in subjects suffering from fibrodysplasia ossificans progressiva. Previous clinical studies for the treatment of fibrodysplasia ossificans progressiva using palovarotene were designed to provide acute therapy during non-quiescent periods with the assumption: (i) that new bone formation would largely occur only immediately following a flare-up; (ii) that treatment commencing within 7 days of the initiation of a flare-up would suffice to reduce or prevent heterotopic ossification; and (iii) that limiting treatment to periods of not more than 6 weeks would be sufficient to prevent heterotopic ossification. The rationale to provide flare-up based treatment is founded on the observation that FOP is a chronic disease characterized by episodes of acute flare-ups that result in new heterotopic ossification formation and progressively worsening disability. Interspersed with periods of flare-up activity (i.e., non-quiescent periods) are variable-length intervals of apparent disease quiescence in which clinical symptoms are not present, and during which it was not known whether bone formation was occurring or not.

These studies have shown that commencing treatment within 7 days of the initiation of a flare-up can be too late to significantly reduce heterotopic ossification as the bone formation process may be initiated before flare-up symptoms are recognized. Furthermore, the study results suggest that chronic treatment may be needed to ensure that the subject is benefitting from palovarotene treatment at the time when the bone formation process is being initiated, during and after the flare-up is initiated. Finally, the study results suggest that short term treatment (i.e., treatment limited to a 6-week period) can be insufficient as in some subjects as new heterotopic ossification was apparent after 6 weeks (but not seen during the treatment period).

Finally, we observed no adverse effects on the growth plate as detected by knee and hand/wrist radiographs in children undergoing the acute, 6-week treatment; suggesting that longer treatment regimens in children may be feasible.

The present invention can improve upon the earlier treatment protocols by (i) providing palovarotene administered chronically (i.e., daily) during quiescent periods; (ii) increasing the dosing level during non-quiescent periods following flare-ups; and (iii) extending the dosing duration during non-quiescent periods to reduce late-emerging new heterotopic ossification. Administering treatment daily during quiescent periods (e.g., 5 mg daily), with more intensive treatment at the time of a flare-up (e.g., higher dose administration of 20 or 10 mg daily, for 84, 112 or 140 days after initiation of a flare-up), can ensure exposure to palovarotene throughout the disease process, and can improve the treatment benefit for FOP patients.

I. Fibrodysplasia Ossificans Progressiva (FOP)

The dosing regimens of palovarotene described herein reduce muscle damage and heterotopic ossification in a subject with FOP. Palovarotene (also called 4-[(1E)-2-[5,6,7,8-Tetrahydro-5,5,8,8-tetramethyl-3-(1H-pyrazol-1-ylmethyl)-2-naphthalenyl]-ethenyl]-benzoic acid) is a retinoic acid receptor gamma (RARγ) selective agonist having the structure:

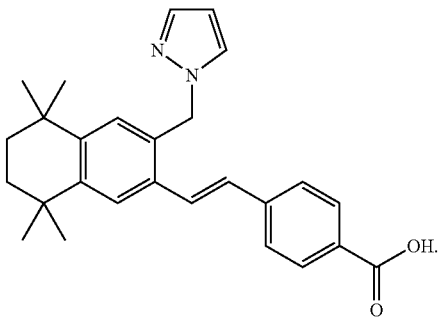 [SMILES: CC1(C)CCC(C)(C)c2cc(Cn3cccn3)c(/C=C/c3ccc(C(=O)O)cc3)cc21]

In some embodiments, palovarotene is administered under the dosing regimens described herein to a subject with FOP. FOP is a rare, severely disabling disease characterized by painful, recurrent episodes of soft tissue swelling (flare-ups) and abnormal heterotopic ossification (HO) in muscles, tendons, and ligaments. Flare-up symptoms, their progression and frequency in FOP patients have been described in detail (e.g. Pignolo, R. J. et al. J. Bone Miner. Res. 31, 650-656 (2016)).

In some embodiments, lesions begin in early childhood and lead to progressive ankyloses of major joints with resultant loss of movement. Prognosis is poor and median life expectancy is 40 years. FOP is caused by an activating mutation in the bone morphogenetic protein (BMP) type I receptor, or activin receptor type 1A (ACVR1), also known as activin-like-kinase 2 (ALK2) type I receptor. Most patients with FOP have the same point mutation, R206H, termed classical FOP, although roughly 3% of patients have other mutations in the same gene. The prevalence is estimated at approximately 1 in 2 million individuals, with no geographic, ethnic, racial, or gender preference. Heterotopic ossification is episodic and cumulative throughout life, resulting in segments, sheets, and ribbons of extra bone developing throughout the body and across joints, progressively restricting movement. Rapidly growing bony spurs have been known to protrude through the skin causing pain and a risk of infections. Asymmetric HO in the rib cage and subsequent contralateral growth can lead to a rapid progression in spinal deformity and cause thoracic insufficiency syndrome. Ankyloses of the temporomandibular joints results in severe tooth decay and malnutrition.

As described in Example 3, the presence of muscle necrosis as detected by imaging may indicate an increased risk of HO formation. In addition, the presence of substantial muscle necrosis in some subjects observed in imaging performed within 7 days of flare-up symptom onset suggest that the process that ultimately leads to new HO formation may start before clinical symptoms are reported. Based on these observations, in some embodiments, it may be helpful to provide a non-flare-up based dosing in order to provide exposure to palovarotene when the process initiates, and before clinical symptoms are evident.

In some embodiments, periods of flare-up activity are interspersed with variable-length intervals of apparently quiescent disease in the absence of obvious clinical symptoms.

In a patient with FOP heterotopic ossification (HO) can be measured using a variety of methods known in the art including but not limited to low dose CT-scan imaging, magnetic resonance imaging (MRI) and X-ray imaging. One clinically relevant measure of HO in FOP is the proportion of flare-ups in a patient with no new HO, the number of flare-ups or non-quiescent periods experienced by a patient over a given time-period that do not result in new heterotopic bone formation.

II. Pharmaceutical Composition and Formulation

For administration to a subject, palovarotene can be provided in pharmaceutically acceptable compositions. These pharmaceutically acceptable compositions include palovarotene and one or more pharmaceutically acceptable carriers and excipients. Pharmaceutical compositions may be formulated for administration in solid or liquid form.

The palovarotene can be administered in neutral form (i.e., the free base or zwitterionic neutral form). Optionally, palovarotene may be administered as a pharmaceutically acceptable salt, such as a non-toxic acid addition salts or metal complexes that are commonly used in the pharmaceutical industry. Examples of acid addition salts that could be used in the methods of the invention include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes that could be used in the methods of the invention include calcium, zinc, and iron, among others.

In some embodiments, a pharmaceutical composition including palovarotene is prepared for oral administration. In some embodiments, a pharmaceutical composition is formulated by combining palovarotene with one or more pharmaceutically acceptable carriers and excipients. Such carriers and excipients enable the pharmaceutical composition to be formulated as tablets, pills, dragees, capsules, liquids, gels, syrups, slurries, and suspensions, for oral ingestion by a subject.

In some embodiments, pharmaceutical compositions for oral use are obtained by mixing palovarotene and one or more carriers and excipients. Suitable carriers and excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, such a mixture is optionally ground and auxiliaries are optionally added. In some embodiments, pharmaceutical compositions are formed to obtain tablets or dragee cores. In some embodiments, disintegrating agents (e.g., cross-linked polyvinyl pyrrolidone, agar, or alginic acid or a salt thereof, such as sodium alginate) are added.

When palovarotene is administered orally, a pharmaceutical composition containing palovarotene may be in unit dosage form (e.g., liquid or solid unit dosage form). The concentration and/or amount of palovarotene in the formulation may vary depending on, e.g., the dosage of palovarotene to be administration and the frequency of administration.

III. Therapy and Dosage

Palovarotene may be administered to a subject with FOP regardless of whether the subject is experiencing a flare-up. For example, a non-flare-up based dosing (i.e., administering palovarotene during quiescent periods) may provide the subject with exposure to palovarotene when the flare-up process initiates, and before clinical symptoms are evident. In some embodiments, palovarotene may be administered to a subject with FOP chronically (e.g., chronic daily treatment during quiescent and non-quiescent periods). In some embodiments, palovarotene may be administered to a subject with FOP chronically (e.g., chronic daily treatment during quiescent periods) and the dosage of palovarotene may be increased during flare-ups (e.g., acute daily treatment during non-quiescent periods, or for a period following initiation of a non-quiescent period from 84 days to 112 or 140 days in length during which there is risk of further heterotopic ossification).

The end of the non-quiescent treatment period is marked by a reduction in the risk of heterotopic ossification in some cases 84 days following the initiation of non-quiescent period treatment, i.e., 84 days following occurrence of flare-up symptoms. If a patient subject experiences persistent flare-up symptoms, the non-quiescent treatment period can be extended by, e.g., another 28 days or 56 days. During the non-quiescent period the subject can be treated with higher daily doses of palovarotene (i.e. loading doses and/or maintenance doses). At the end of the non-quiescent period, the subject can return to treatment with lower daily doses of palovarotene administered during quiescent periods. The determination about when to transition from non-quiescent dosing to quiescent dosing, i.e. the end of the non-quiescent period, depends upon, and can be defined by, the symptoms experienced by the subject, a determination that can be made in consultation with a subject's care provider or by the patient alone. In the dosing regimens of the invention, the subject can return to a non-quiescent dosing level after the subject has not experienced flare-up symptoms for at least 2 weeks, 3 weeks, 4 weeks, or 5 weeks consecutively.

In some embodiments 5 mg daily is administered to a subject during quiescent periods, 20 mg daily is administered for 28 days following initiation of a non-quiescent period followed by 10 mg daily for 56 days and returning to a dose of 5 mg per day if the patient is no longer experiencing any flare-up symptoms. Optionally treatment with 10 mg daily can be extended for an additional 28 days or 56 days if the patient continues to experience flare-up symptoms (i.e., the non-quiescent period persists).

Palovarotene dosing regimens of the inventions comprise administering a higher dose following initiation of a non-quiescent phase a loading dose e.g. 20 mg/day for 28 days followed by a maintenance dose e.g. 10 mg/day for 56 days and administering a lower dose during quiescent periods e.g. 5 mg/day. Adult loading doses for use in the treatment regimens of the invention are from 15 to 20 mg/day and may be adjusted based on patient weight or palovarotene tolerability in a patient. Adult maintenance doses for use in the treatment regimens of the invention are from 7.5 to 10 mg/day and may be adjusted based on patient weight or palovarotene tolerability in a patient.

In some embodiments, palovarotene is co-administered with one or more other pharmaceutical agents including, but not limited to, glucocorticoids for managing flare-up symptoms, non-steroidal anti-inflammatory medications, cyclooxygenase-2 inhibitors, leukotriene inhibitors and mast cell stabilizers, aminobisphosphonates, and imatinib mesylate (see Briggs et al., Expert Opinion on Orphan Drugs 3:1137-1154 (2015) and Kaplan et al., Clin Proc Intl Clin Consort FOP 4:1-100 (2011)). In some embodiments, such one or more other pharmaceutical agents are designed to treat the same disease or condition as palovarotene. In some embodiments, such one or more other pharmaceutical agents are designed to treat a different disease or condition as palovarotene. In some embodiments, such one or more other pharmaceutical agents are designed to treat an undesired effect of palovarotene. In some embodiments, palovarotene and one or more other pharmaceutical agents are administered at the same time. In some embodiments, palovarotene and one or more other pharmaceutical agents are administered at different times. In some embodiments, palovarotene and one or more other pharmaceutical agents are prepared together in a single formulation. In some embodiments, palovarotene and one or more other pharmaceutical agents are prepared separately.

Typically, palovarotene is administered in the form of a dosage unit (e.g., tablet, capsule, etc.). In some embodiments, palovarotene is administered in a dose selected from 1.5 mg, 2 mg, 2.5 mg, 3 mg, 4 mg, 5 mg, 6 mg, 7.5 mg, 10 mg, 12.5 mg, 15 mg, or 20 mg.

In some embodiments, the dose can be administered at intervals ranging from more than once per day (e.g., twice per day or three times per day) to once daily, for as long as needed to sustain the desired effect.

EXAMPLES

Example 1—Flare-Up Outcomes

Figure 2:
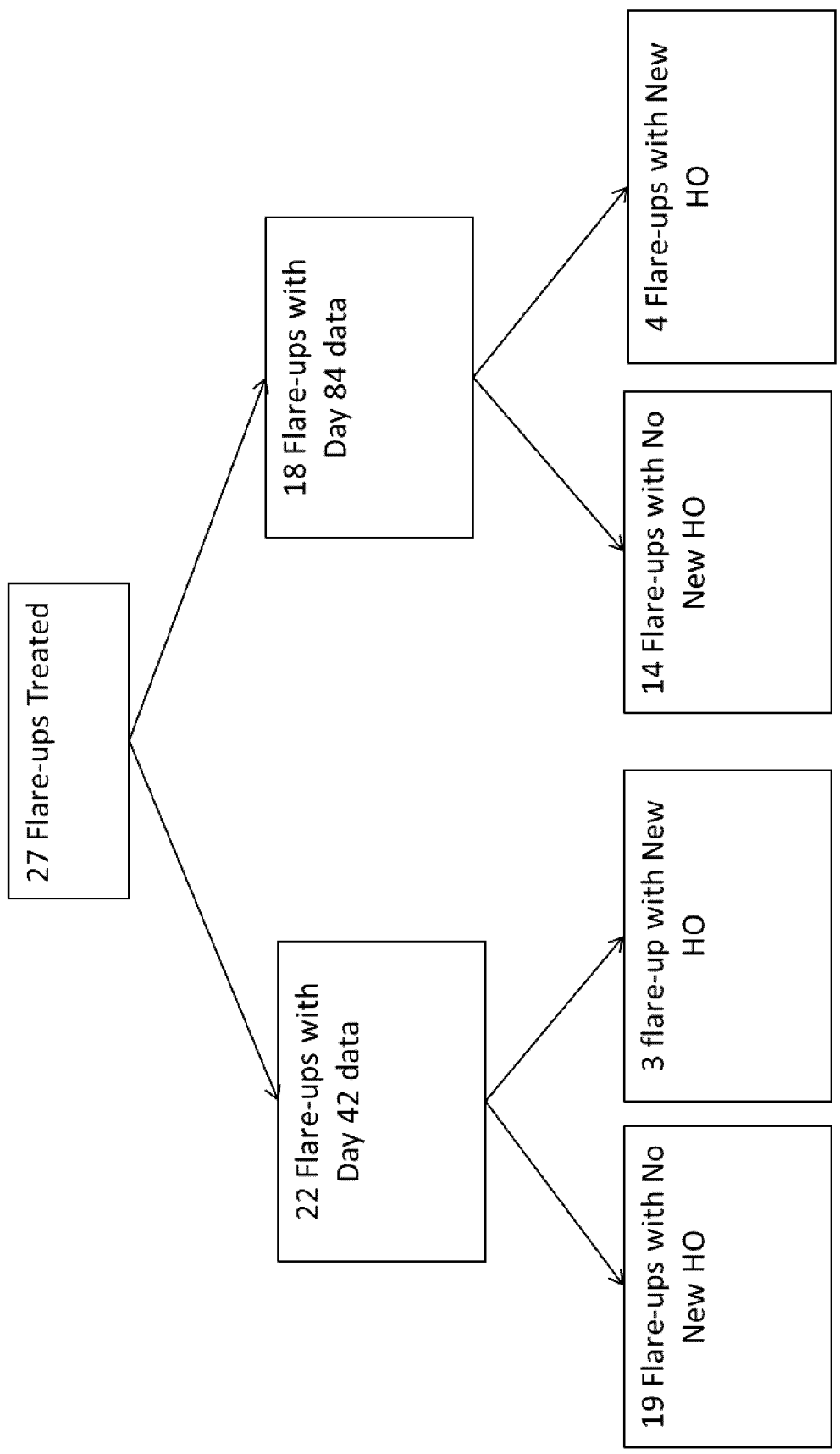
FIG. 2 is a chart displaying flare-up outcomes from open-label study including 27 subjects.

Sixty-seven flare-ups have been treated: 40 with double-blind medication (10 subjects received placebo, 9 subjects received palovarotene at 5 mg once daily for 2 weeks followed by 2.5 mg once daily for 4 weeks, and 21 subjects received palovarotene at 10 mg once daily for 2 weeks followed by 5 mg once daily for 4 weeks); and 27 received open-label palovarotene. Sixty-one of these 67 flare-ups have available results from post-baseline imaging (by low-dose CT scan). The results are summarized for the respective studies in FIGS. 1 and 2.

New HO was observed in 14 of 61 flare-ups, ten in the double-blind study and four in the open-label extension study. The majority of these flare-ups (10 of 14) resulted in new HO at the end of the 6-week treatment (Day 42), and four resulted in new HO at the end of the 6-week follow-up (Day 84).

Example 2—Palovarotene Dosing Regimen for Adult Cohort

Adult cohort includes individuals who have achieved at least 90% skeletal maturity irrespective of age. Individuals in the adult cohort received palovarotene (neutral form) at 5 mg once daily as a non-flare-up based treatment (e.g., during periods when symptoms of a flare-up were not present). This dosing regimen ensured that subjects were exposed to palovarotene when the HO process began, prior to the presence of clinical symptoms.

Figure 3A:
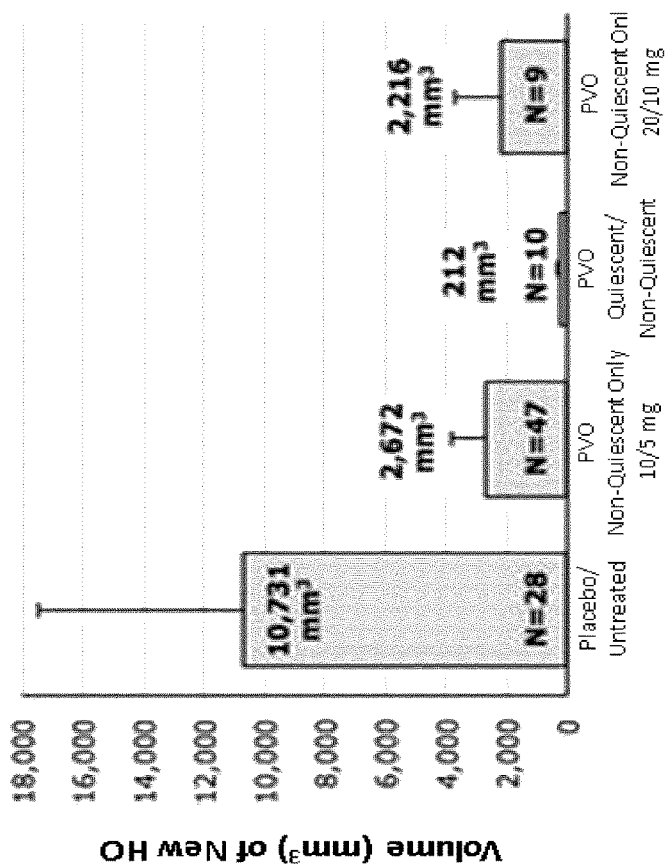
FIGS. 3A and 3B are graphs showing a comparison of the volume of new heterotopic ossification between (i) episodic treatment of FOP patients (i.e., treatment during non-quiescent periods only and (ii) the treatment regimens of the present invention that include treatment during both quiescent and non-quiescent periods. Patients in the "Placebo/Untreated" group were treated with a sugar pill or untreated (28 patients). Patients in the "PVO Non-Quiescent Only" group were treated with either 20 mg palovarotene (PVO) daily for 28 days followed by 10 mg PVO daily for 56 days (47 patients) or 10 mg PVO daily for 14 days followed by 5 mg PVO daily for 28 days (9 patients). Patients in the "PVO Quiescent/Non-Quiescent" group were treated with 5 mg PVO daily during the quiescent period and with 20 mg PVO daily for 28 days (NQ loading dose) followed by 10 mg PVO daily for 56 days (NQ maintenance dose) following initiation of flare-up symptoms, i.e., initiation of a non-quiescent period (10 patients).

Individuals in the adult cohort who experienced a flare-up received increased dosing with palovarotene at 20 mg once daily for 28 days, followed by 10 mg once daily for at least 56 days (a total of 3 months treatment). Treatment was extended by 4-week increments if the flare-up was ongoing at the end of the original 3-months. When the flare-up had resolved, subjects returned to the non-flare-up based treatment of 5 mg. Ten individuals received this treatment ("PVO Quiescent/Non-Quiescent" treatment: 5 mg PVO daily during the quiescent period, and 20 mg PVO daily for 28 days (NQ loading dose) followed by 10 mg PVO daily for 56 days (NQ maintenance dose) following initiation of flare-up symptoms). Outcomes were compared to those of individuals treated with a sugar pill or untreated ("Placebo/Untreated", 28 patients), and to individuals treated with either 20 mg palovarotene (PVO) daily for 28 days followed by 10 mg PVO daily for 56 days (47 patients) or 10 mg PVO for 14 days followed by 5 mg PVO for 28 days (9 patients) during a non-quiescent period (i.e., "PVO Non-Quiescent Only" group in FIG. 3A).

Assessment of new HO at the flare-up site was evaluated using x-ray, and low-dose CT imaging was employed as a secondary imaging assessment. Interpretation of the radiographs and CT scans included assessment for the absence or presence of new HO at the flare-up site compared with the baseline image, and the volume of new HO, if present. Performing both x-ray and CT scans of the flare-up site allowed for the selection of the most appropriate method for evaluation of HO, assisting with the design of subsequent studies. In order to ensure consistency and standardization, images were evaluated for the presence or absence of HO using two independent procedures, both of which were blinded to treatment group assignment. In the Primary Read process, two musculoskeletal radiologists independently compared baseline and post-baseline images within a single imaging modality.

Figure 3B:
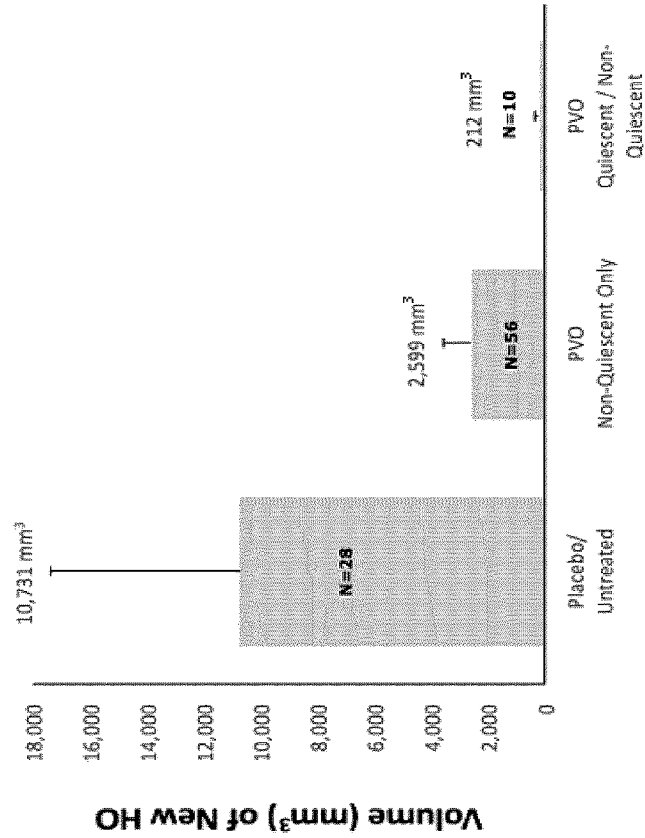

The volume of new heterotopic ossification (HO), HO that occurred during the non-quiescent period, was assessed 12 weeks following initiation of treatment for the "Non-Quiescent Only" treatment group and 12 weeks after initiation of the 20 mg/day NQ loading dose in the "Quiescent/Non-Quiescent" treatment group. These data indicate that the "Quiescent/Non-Quiescent" treatment regimen further inhibits new bone formation after flare-ups. Relative to the "Placebo/Untreated" group the patients in the "Non-Quiescent Only" group had a 75% reduction in mean bone volume formation (new HO) and patients in the "Quiescent/Non-Quiescent" group had a 97% reduction in mean bone volume formation (new HO) (see FIGS. 3A and 3B). These data also show that "Quiescent/Non-Quiescent" treatment regimens of the invention greatly reduced mean bone volume formation (new HO) compared to "Non-Quiescent Only" treatment (i.e., only treating flare-ups in subjects).

Example 3—Palovarotene Dosing Regimen for Pediatric Cohort

Pediatric cohort includes individuals under 18 who have not achieved 90% skeletal maturity as determined by hand/wrist radiographs. Individuals in the pediatric cohort who experience a flare-up receive palovarotene (neutral form) at 20 mg once daily (or a weight adjusted equivalent dose as shown in Table 1) for 28 days, followed by 10 mg once daily (or a weight adjusted equivalent dose as shown in Table 1) for at least 56 days (a total of 3 months treatment). Treatment may be extended by 4-week increments if the flare-up is ongoing at the end of the original 3-months. In addition to treatment following flare-up symptoms, i.e., during a non-quiescent period, pediatric patients can be treated chronically during a quiescent period, (i.e., when the patient is not experiencing and flare-up symptoms or has not experienced flare-up symptoms within at least the last, e.g., 2 weeks, 4 weeks, 6 weeks, 8 weeks, or 84 days) with between 2.5 and 5 mg paloverotene once daily.

TABLE 1

Weight-Adjusted Dosing Levels for Pediatric Patients (Under 18 and skeletal maturity ≤ to 90%)

| Weight Group (≤90% Skeletal Maturity) | Daily Non-quiescent (NQ) Loading Dose | Daily NQ Maintenance Dose | Daily Quiescent (Q) Dose |
|---|---|---|---|
| 10 to <20 kg | 10 mg | 5 mg | 2.5 mg |
| 20 to <40 kg | 12.5 mg | 6 mg | 3 mg |
| 40 to <60 kg | 15 mg | 7.5 mg | 4 mg |
| ≥60 kg | 20 mg | 10 mg | 5 mg |

Example 4—Safety Outcomes

The overall incidence of adverse events in the double-blind study described in Example 1 was 97.1% (33 of 34 subjects with available safety data), with dose-related increases across the treatment groups. There were also dose-related increases in the incidence and severity of retinoid-associated adverse events. Most retinoid-associated adverse events were mild or moderate in severity. The most frequently reported adverse events overall were dry skin (58.8%) and dry lips (32.4%). There were no dose reductions or discontinuations of treatment.

The findings were similar in the open-label study (described in Example 1) in which the overall incidence of adverse events was 92.3% (12 of 13 subjects). Retinoid-associated adverse events were reported by all subjects; most were mild (69.2%) in severity. The most frequently reported adverse events overall were dry skin (69.2%) and pruritus (61.5%). There were no dose reductions or discontinuations of treatment.

Example 5—Growth Plate Assessment

The effects of palovarotene on the growth plates were assessed. Daily palovarotene dosing reversed histologic growth plate abnormalities and shortened long bones observed in Prrx1-R206H mice. In this model, histologic analysis revealed significant reduction in the height of the growth plate hypertrophic zone, a region primarily responsible for long bone elongation. Palovarotene treatment preserved long bone growth and near-normalized growth plate organization and matrix deposition in Prrx1-R206H mice. These results suggest opposing effects of palovarotene on growth plate in normal and mutant (ACVR1 R206H) cells and tissues. Adverse effects of palovarotene in wild-type mice are in contrast with the beneficial effects observed in FOP mice.

Example 6—Alternative Dosing Regimens

For individuals experiencing tolerance problems, an alternative de-escalated dosing regimen can be employed as provided in Tables 2 and 3. The quiescent period (Q) dosing level is administered chronically during the quiescent period (e.g., when patient is not experiencing flare-up or to individuals who have not experienced flare-up symptoms for at least 4 weeks consecutively). The non-quiescent (NQ) dosing level is administered during non-quiescent period. Non-quiescent period (NQ) loading dose is administered for 20 to 40 days (e.g., 21 to 30 days, or 28 days) following initiation of a flare-up (e.g., within 7 days of patient experiencing one or more symptoms of flare-up). The NQ maintenance dosing level is administered immediately following the NQ loading dose for a period of at least 56 days and can be extended beyond 56 days in 4 week increments, e.g., 4, 8 or 12 weeks, if patient's flare-up symptoms persist until symptoms of flare-up resolve.

TABLE 2

Dosing Levels for Adult Patients

| Adult Weight Group (>18 or <18 with >90% skeletal maturity) | Daily Non-quiescent (NQ) Loading Dose | Daily NQ Maintenance Dose | Daily Quiescent (Q) Dose |
| --- | --- | --- | --- |
| Standard Adult Dosing | 20 mg | 10 mg | 5 mg |
| De-escalated Adult Dosing 1 | 15 mg | 10 mg | 5 mg |
| De-escalated Adult Dosing 2 | 10 mg | 10 mg | 5 mg |
| De-escalated Adult Dosing 3 | 15 mg | 7.5 mg | 4 mg |

TABLE 3

Weight-Adjusted Dosing Regimens for Children (Under 18 and skeletal maturity ≤ to 90%)

| Weight Group (≤90% Skeletal Maturity) | Daily Non-quiescent (NQ) Loading Dose | Daily NQ Maintenance Dose | Daily Quiescent (Q) Dose |
| --- | --- | --- | --- |
| 10 to <20 kg Regimen | 10 mg | 5 mg | 2.5 mg |
| 10 to <20 kg De-Escalation Regimen | 7.5 mg | 3 mg | 1 mg |
| 20 to <40 kg Regimen | 12.5 mg | 6 mg | 3 mg |
| 20 to <40 kg De-Escalation Regimen | 10 mg | 5 mg | 2.5 mg |
| 40 to <60 kg Regimen | 15 mg | 7.5 mg | 4 mg |
| 40 to <60 kg De-Escalation Regimen | 12.5 mg | 6 mg | 3 mg |
| ≥60 kg Regimen | 20 mg | 10 mg | 5 mg |
| ≥60 kg De-Escalation Regimen | 15 mg | 7.5 mg | 4 mg |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

What is claimed:

1. A method of reducing heterotopic ossification in a subject with fibrodysplasia ossificans progressiva, said method comprising: (i) during a period when the subject is not experiencing any flare-up symptom orally administering daily to the subject an amount of 5±0.5 mg of palovarotene, or a pharmaceutically acceptable salt thereof, and (ii) during a period when the subject is experiencing at least one flare-up symptom orally administering to the subject an amount of 20±1.0 mg of palovarotene, or a pharmaceutically acceptable salt thereof, daily for a period of 20 to 40 days, and after the period of 20 to 40 days, and amount of 10±1.0 mg of palovarotene, or a pharmaceutically acceptable salt hereof, daily for a period of 14 to 112 days.

2. The method of claim 1, wherein the 10±1.0 mg amount is administered daily for a period of 14 to 84 days.

3. A method of reducing heterotopic ossification in a subject with fibrodysplasia ossificans progressiva, said method comprising: (i) during a period when the subject is not experiencing any flare-up symptom orally administering daily to the subject an amount of 5 mg of palovarotene, or a pharmaceutically acceptable salt thereof, and (ii) during a period when the subject is experiencing at least one flare-up symptom orally administering daily to the subject an amount of 20 mg of palovarotene, or a pharmaceutically acceptable salt thereof, for 28 days, and after the 28 days, orally administering daily to the subject an amount of 10 mg of palovarotene, or a pharmaceutically acceptable salt thereof, for at least 56 days.

4. The method of claim 1, wherein the 10±1.0 mg amount is administered daily for a period of 84 days.

5. The method of claim 1, wherein the 10±1.0 mg amount is administered daily for a period of 14 to 56 days.

6. The method of claim 1, wherein the 10±1.0 mg amount is administered daily for a period of 56 days.

7. The method of claim 1, wherein the 10±1.0 mg amount is administered daily for a period of 56 days, and for an additional 28 days if the subject continues to experience at least one flare-up symptom.

8. The method of claim 1, wherein the 10±1.0 mg amount is administered daily for a period of 112 days.

9. The method of claim 1, wherein the 20±1.0 mg amount is administered daily for a period of 28 ±4 days.

10. The method of claim 1, wherein the 20±1.0 mg amount is administered daily for a period of 28 days.

11. The method of claim 1, wherein the subject weighs greater than 60 kg.

12. The method of claim 1, wherein the subject has a skeletal maturity of 90% or greater.

13. The method of claim 1, further comprising administering to the subject an antihistamine.

14. The method of claim 13, wherein the antihistamine is administered topically.

15. The method of claim 13, wherein the antihistamine is administered systemically.

16. The method of claim 1, further comprising administering to the skin of the subject an emollient.

17. The method of claim 1, wherein the at least one flare-up symptom is chosen from swelling, pain, erythema, warmth, stiffness, and decreased range of motion.

18. The method of claim 1, wherein the daily amount is of palovarotene.

19. The method of claim 1, wherein the daily amount is of a pharmaceutically acceptable salt of palovarotene.

20. The method of claim 3, wherein the 10 mg daily amount is administered for 56 days.

21. The method of claim 3, wherein the 10 mg daily amount is administered for 56 days and for an additional 28 days if the subject continues to experience at least one flare-up symptom.

22. The method of claim 3, wherein the subject weighs greater than 60 kg.

23. The method of claim 3, wherein the subject has a skeletal maturity of 90% or greater.

24. The method of claim 3 further comprising administering to the subject an antihistamine.

25. The method of claim 24, wherein the antihistamine is administered topically.

26. The method of claim 24, wherein the antihistamine is administered systemically.

27. The method of claim 3, further comprising administering to the skin of the subject an emollient.

28. The method of claim 3, wherein the at least one flare-up symptom is chosen from swelling, pain, erythema, warmth, stiffness, and decreased range of motion.

29. The method of claim 3, wherein the daily amount is of palovarotene.

30. The method of claim 3, wherein the daily amount is of a pharmaceutically acceptable salt of palovarotene.

* * * * *